(12) United States Patent
Baird et al.

(10) Patent No.: US 8,889,894 B2
(45) Date of Patent: Nov. 18, 2014

(54) COMPOUNDS FOR USE IN THERAPY

(75) Inventors: Mark Stephen Baird, Gwynedd (GB); Juma' a Raheem Najeem Al-Dulayy-mi, Gwynedd (GB); Cornelias Theunissen, Gwynedd (GB); Gani Koza, Gwynedd (GB); Seppe Vander-Beken, Ghent (BE); Johan Adriaan Marc Grooten, Ghent (BE)

(73) Assignees: Bangor University, Gwynedd (GB); Universiteit Gent, Ghent (BE)

( * ) Notice: Subject to any disclaimer, the term of this patent is extended or adjusted under 35 U.S.C. 154(b) by 645 days.

(21) Appl. No.: 12/988,235

(22) PCT Filed: Apr. 22, 2009

(86) PCT No.: PCT/GB2009/050408
§ 371 (c)(1),
(2), (4) Date: Mar. 3, 2011

(87) PCT Pub. No.: WO2009/130506
PCT Pub. Date: Oct. 29, 2009

(65) Prior Publication Data
US 2011/0150981 A1    Jun. 23, 2011

(30) Foreign Application Priority Data
Apr. 22, 2008 (GB) .................... 0807305.8

(51) Int. Cl.
*C07C 59/185* (2006.01)
*C07C 61/04* (2006.01)
(Continued)

(52) U.S. Cl.
CPC ............... *A61K 31/00* (2013.01); *C07C 59/185* (2013.01); *A61K 9/0073* (2013.01);
(Continued)

(58) Field of Classification Search
None
See application file for complete search history.

(56) References Cited

U.S. PATENT DOCUMENTS

2007/0027098 A1    2/2007    Raz et al.

OTHER PUBLICATIONS

Yuan, Y., et al., A common mechanism for the biosynthesis of methoxy nd cyclopropyl mycolic acids in *Mycobacterium tuberculosis*, Nov. 1996, Proc.Natl. Acad. Sci. USA, vol. 93, pp. 12828-1833.*

(Continued)

*Primary Examiner* — Yate K Cutliff
(74) *Attorney, Agent, or Firm* — Norris McLaughlin & Marcus PA

(57) ABSTRACT

A compound of formula (I) for use in the treatment of a disease of the immune system; wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkenylene, arylene, alkylarylene, cycloalkylene, ketone, ester, amide, imide, imine, thioether, ether, thioester and thioketone; and P is selected from hydrogen, an alkyl group, a sugar residue, or a metal, phosphonium or ammonium species; wherein at least one of X, Y and Z includes a moiety selected from cyclopropyl, C=A, C-AH and C—$OR^5$; wherein $R^5$ is alkyl or haloalkyl, and A is O, S or $NR^6$, wherein $R^6$ may be H or 20 alkyl.

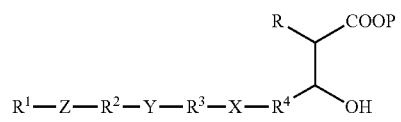

3 Claims, 6 Drawing Sheets

(51) Int. Cl.
- A61K 9/127 (2006.01)
- A61K 31/00 (2006.01)
- A61K 9/00 (2006.01)
- C07C 59/11 (2006.01)
- C07C 59/13 (2006.01)
- C07C 59/215 (2006.01)

(52) U.S. Cl.
CPC .............. *A61K 9/127* (2013.01); *C07B 2200/07* (2013.01); *C07C 59/11* (2013.01); *C07C 59/13* (2013.01); *C07C 59/215* (2013.01); *C07C 2101/02* (2013.01)
USPC ........... 554/115; 554/117; 554/213; 554/214; 562/506; 424/450

(56) References Cited

OTHER PUBLICATIONS

Villeneuve, M., et al., Conformational behavior of oxygenated mycobacterial mycolic acids from *Mycobacterium bovix* BCG, 2007, Biochimica et Biophysica Acta, 1768, pp. 1717-1726.*

Villeneuve, M., et al., Erratum to "Conformational behavior of oxygenated mycobacterial mycolic acids from *Mycobacterium bovis* BCG" [Biochim. Biophys. Acta 1768 (2007) 171-1726], 2007, Biochimica et Biophysica Acta, 1768, pp. 2343.*

Qureshi, N., et al., Characterizatio of the purified components of a new homologus series of alpha-mycolic acids from *Mycobacterum tuberculosis* H37Ra, 1978, J. Biol. CHem., vol. 253, No. 15, issue of Aug. 10, pp. 5411-5417.*

XP025383894, Al Dulayymi J R et al: "The Synthesis of a Single Enantiomer of a Major Appha-Mycolic Acid of *M. tuberculosis*", Tetrahedron, Elseview Science Publishers, Amsterdam, NL, vol. 61, No. 50, pp. 11939-11951, Dec. 2005.

XP025001941, Al Dulayymi J R et al: The Synthesis of One Enantiomer of the Alpha-Methyl-Trans-Cycloprepane Unit of Mycolic Acids:, Tetrahedron, Elseview Science Publishers, Amsterdam, NL, vol. 62, No. 20, pp. 4851-4862, May 2006.

XP004173992, Coxon G D et al: "The Synthesis of Both Enantiomers of Lactobacillic Acid and Mycolic Acid Analogues", Tetrahedron Letters, Elsevier, Amsterdam, NL, vol. 40, No. 36, pp. 6689-6692, Sep. 1999.

XP002546341, Korf Johanna E et al: "Macrophage Reprogramming by Mycolic Acid Promotes a Tolerogenic Reposne in Experimental Asthma", American Journal of Respiratory and Critical Care Medicine, vol. 174, No. 2, pp. 152-160, Jul. 2006.

XP002546342, Asselineau J et al: "Mycobacterial Lipids: A Historical Perspective", Frontiers in Bioscience: A Journal and Virtual Library, vol. 3, pp. 164-174, Oct. 1998.

XP002539259, Parant M et al., Nonspecific Immunostimulant Activities of Synthetic Trehalose-6, 6'-diesters (lower homologs of cord factor): Infection and Immunity, vol. 20, No. 1, Apr. 1978.

XP002539260, Bekierkunst A et al: "Immuno Therapy of Cancer with Nonliving BCG and Fractions Derived from Mycobacteria Role of Cord Factor Trealose 6 6 Di Mycolate in Tumor Regression" Infection and Immunity, vol. 10, No. 5, pp. 1044-1050, 1974.

XP022590789, Benadie Y et al: "Cholesteroid Nature of Free Mycolic Acids from *M. tuberculosis*" Chemistry and Physics of Lipids, Limerick, IR, vol. 152, No. 2, pp. 95-103, Apr. 2008.

The First Synthesis of Single Enantiomers of Ketomycolic Acids G. Koza and M.S. Baird, Tetrahedron Letters, (2007), 48, 2165-2169.

Temperature Dependence of the Langmuir Momolayer Packing of Mycolic Acids from *Mycobacterium tuberculosis* M. Villeneuve et al, Biochimica et Biophysica Acta, (2005), 1715(2), 71-80.

Pulmonary Granulomas of Guinea Pigs Induced by Inhalation Exposure of Heat-Treated BCG Pasteur Purified Trehalose Dimycolate and Methyl Ketomycolate, I. Sugawara et al., J. Med. Microbiol, (2002), 51(2), 131-137.

The Specificity of Methyl Transferases Involved in Trans Mycolic Acid Biosynthesis in *Mycobacterium tuberculosis* and *Mycobacterium smegmatis*, B.G. Schroeder and C.E. Barry, Bioorganic Chemistry, (2001) 29, 164-177.

The Effect of Oxygenated Mycolic Acid Composition on Cell Wall Function and Macrophage Growth in *Mycobacterium tuberculosis* Y. Yuan et al, Molecular Microbiology (1998), 29(6), 1449-1458.

"Synthetic Mirror Cord Factors: Proctected Dimycolyl Esters of an a, a -)1-1)-bisheptosiduronic acid" H.H. Baer and X. Wu, Carbohydrate Research, (1993), 245. 347-352.

"Characterization of the Purified Components of a New Homologous Seriers of Alpha-Mycolic Acids from *Mycobacterium tuberculosis* H37Ra*", N. Qureshi and K Takayama, The Journal of Biological Chemistry, (1978), 253 (15), 5411-5417.

"Structure of Mycolic Acids and of an Intermediate in the Biodynthesis of Dicarboxylic Mycolic Acids", M.A. Laneelle and F. Laneelle, Eurpoean Journal of Biochemistry, (1970), 12(2), 296-300.

Structure of an Arabinose Dimycolate Isolated from *Mycobacterium marianum*, M. Bruneteau & G. Michel, Chemistry and Physics of Lipids, (1968), 2(3), 229-239.

"Structureal Studies on the Mycolic Acids", D.E. Minnikin and N. Polgar, Chemical Communications (London), (1967), 7, 312-314.

M. Watanabe, et al, "Location of functional groups in mycobacterial meromycolate chains; the recognition of new structural principles in mycolic acids", Microbiology (2002), 148, pp. 1881-1902.

M. Watanabe, et al, "Separation and characterization of individual mycolic acids in representative mycobacteria", Microbiology (2001), 147, pp. 1825-1837.

J.R. Al Dulayymi, et al, "The synthesis of a single enantiomer of a major α-mycolic acid of *Mycobacterium tuberculosis*", Chem Commun (Camb) 2003, pp. 228-229.

J.R. Al Dulayymi, et al, "The synthesis of a single enantiomer of a major α-mycolic acid of *M. tuberculosis*", Tetrahedron 61, 2005, pp. 11939-11951.

J.R. Al Dulayymi, et al, "The first synthesis of single enantiomers of the major methoxymycolic acid of *Mycobacterium tuberculosis*", Tetrahedron 63, 2007, pp. 2571-2592.

J.R. Al Dulayymi, et al, "The synthesis of single enantiomers of meromycolic acids from mycobacterial wax esters", Tetrahedron 62, 2006, pp. 11867-11880.

J.R. Al Dulayymi, et al, "The synthesis of one enantiomer of the α-methyl-trans-cyclopropane unit of mycolic acids", Tetrahedron 62, 2006, pp. 4851-4862.

Koza G, et al, "The first synthesis of single enantiomers of ketomycolic acids", Tetrahedron Letters 48, 2007, pp. 2165-2169.

Toschi G, et al, "An improved procedure for the preparation of the (β-hydroxy-α-alkyl fatty acid fragment of mycolic acids",Tetrahedron 62, 2006, pp. 3221-3227.

Korf J. et al, "The *Mycobacterium tuberculosis* cell Wall Component mycolic acid elicits pathogen-associated host innate immune responses", Eur. J. Immunol 2005:35:890-900.

Korf et al, "Macrophage Reprogramming by Mycolic Acid Promotes a Tolergenic Response in Experimental Asthma", Am. J. Respir, Crit. Care Med., vol. 174, pp. 152-160, 2006.

* cited by examiner

COMPOUNDS FOR USE IN THERAPY

This is an application filed under 35 USC 371 of PCT/GB2009/050408.

The present invention relates to mycolic acid-derived compounds and to methods and uses relating thereto.

Mycolic acids are long chain fatty acid compounds typically having 60 to 90 carbon atoms and are found in the cell walls of mycobacteria. An example of such bacteria is *Mycobacterium tuberculosis*.

Two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in FIG. A), can be differently substituted in both the proximal (the one nearer the hydroxy-acid) and the distal position (further from the carboxylic acid). The mycolic acids are broadly separated into classes, according to the groups present in the meromycolate moiety. The proximal or distal functional groups can be cyclopropanes, double bonds, an epoxy group, a methoxy group, carbonyl group, carboxyl group or methyl group.

Details of the many different compounds that are found in natural sources of mycolic acid are given by M Watanabe, Y Aoyagi, H Mitome, T Fujita, H Naoki, M Ridell and D E Minnikin, *Microbiology* (2002), 148, 1881-1902; and M Watanabe, Y Aoyagi, Malin Ridell and D E Minnikin; *Microbiology* (2001), 147, 1825-1837.

Examples of the general structure of some sub-classes of mycolic acids are shown in FIG. A:

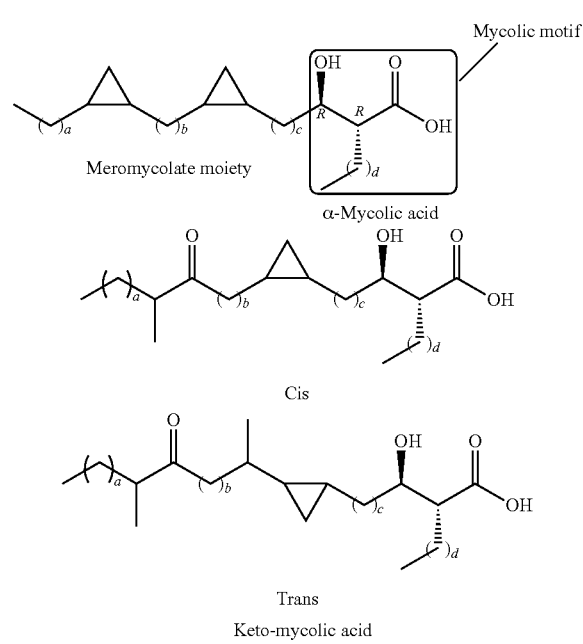

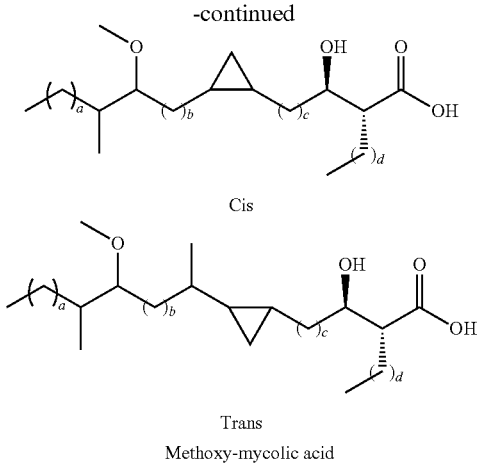

Natural sources of mycolic acids, for example the cell walls of mycobacteria such as *Mycobacterium tuberculosis* include mixtures of different classes of compounds and different homologues. Separation of these compounds is a tedious undertaking and thus very little is known about the properties of the individual separated components. For example, most biological testing carried out previously has been done on mixtures extracted from natural sources of compounds.

The present inventors have prepared synthetic compounds as single stereoisomers of a number of mycolic acids which are identical or closely analogous to single compounds found in the natural mixtures. They have surprisingly found that single compounds representative of certain sub-classes including particular functionalities have advantageous properties compared with other sub-classes or mixtures thereof.

Figures 1A, 1B:
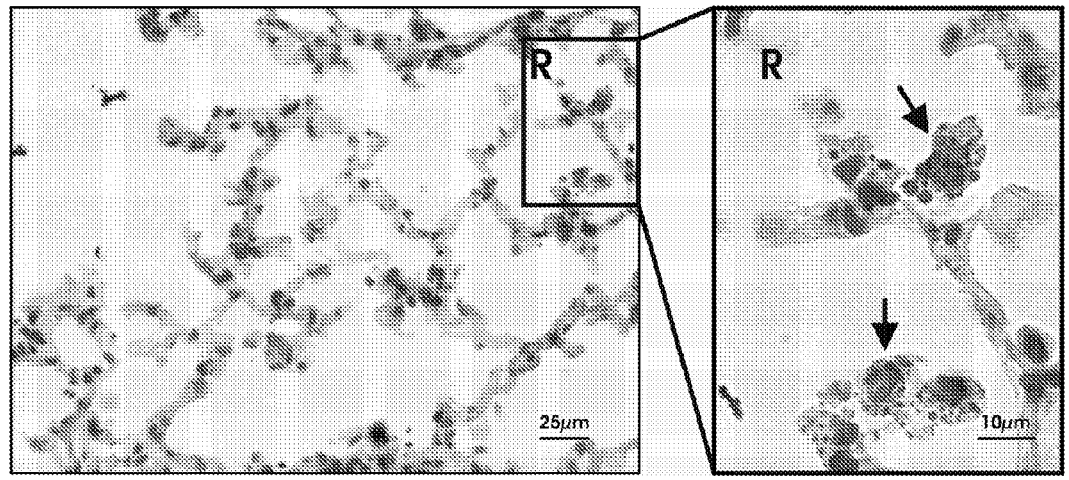
FIG. 1a illustrates a light microscopy image of an ORO-stained lung section of a mouse.
FIG. 1b illustrates a portion of FIG. 1a in a higher magnification.

According to a first aspect of the present invention there is provided a compound of formula I:

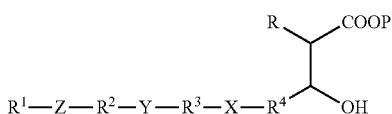

for use in the treatment of a disease of the immune system; wherein R is an optionally-substituted alkyl, alkenyl, alkynyl, aryl, arylalkyl or alkylaryl moiety having from 1 to 50 carbon atoms; $R^1$ is an optionally-substituted alkyl, alkenyl, alkynyl, aryl, arylalkyl or alkylaryl moiety having from 1 to 40 carbon atoms; each of $R^2$, $R^3$ and $R^4$ is independently selected from an optionally-substituted alkylene, alkenylene, alkynylene, arylene, arylalkylene or alkylarylene moiety having from 1 to 40 carbon atoms; each of X, Y and Z is independently selected from an optionally-substituted alkylene, alkenylene, alkynylene, arylene, alkylarylene, cycloalkylene, ketone, ester, amide, imide, imine, thioether, ether, thioester and thioketone; and P is selected from hydrogen, an alkyl group, a sugar residue, or a metal, phosphonium or ammonium species; wherein at least one of X, Y and Z includes a moiety selected from cyclopropyl, C=A, C-AH and C—$OR^5$; wherein $R^5$ is alkyl or haloalkyl, and A is O, S or $NR^6$, wherein $R^6$ may be H or alkyl.

R is preferably an optionally-substituted alkyl, alkenyl, alkynyl, aryl or alkylaryl moiety having from 4 to 40 carbon atoms, preferably from 6 to 36 carbon atoms, for example from 10 to 32 carbon atoms, preferably from 16 to 30 carbon atoms, for example from 18 to 28 carbon atoms, preferably from 20 to 26 carbon atoms. Most preferably R has from 22 to 24 carbon atoms.

R may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably R is an optionally-substituted alkyl or alkenyl group. If R is an alkenyl group, it preferably includes at most one double bond for every six carbon atoms, more preferably at most one double bond for every ten carbon atoms. Any double bonds present may have an E or Z configuration. However in especially preferred embodiments no double bonds are present and R is an alkyl group.

Preferably R is an optionally substituted alkyl or alkenyl moiety which includes no more than one substituent per four carbon atoms, preferably no more than one substituent for every six carbon atoms, preferably no more than one substituent for every ten carbon atoms, and most preferably no more than one substituent for every sixteen carbon atoms in the chain. In especially preferred embodiments, R is an unsubstituted alkyl chain.

Most preferably R is an optionally-substituted alkyl or alkenyl chain. It may be straight chained or branched. Most preferably it is substantially straight chained and any branching is minimal, for example one or two methyl or ethyl residues may be branched from a long main chain. In especially preferred embodiments R is not branched.

Most preferably R is an unsubstituted alkyl chain having from 16 to 30 carbon atoms. In especially preferred embodiments R is an unsubstituted straight chain alkyl group having from 22 to 24 carbon atoms.

$R^1$ is an optionally-substituted alkyl, alkenyl, alkynyl, aryl or alkylaryl moiety having preferably from 4 to 36 carbon atoms, more preferably from 6 to 32 carbon atoms, for example from 8 to 28 carbon atoms, preferably from 10 to 24 carbon atoms, for example from 12 to 22 carbon atoms. Most preferably $R^1$ has from 16 to 20 carbon atoms.

$R^1$ may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^1$ is an optionally-substituted alkyl or alkenyl group. If $R^1$ is an alkenyl group, it preferably includes at most one double bond for every six carbon atoms, more preferably at most one double bond for every ten carbon atoms. Any double bonds present may have an E or Z configuration. However, in especially preferred embodiments, $R^1$ does not contain any double bonds and is an alkyl chain.

Preferably $R^1$ is a substituted alkyl or alkenyl moiety which includes no more than one substituent per four carbon atoms, preferably no more than one substituent for every six carbon atoms, preferably no more than one substituent for every ten carbon atoms, and most preferably no more than one substituent for every twelve carbon atoms in the chain. In especially preferred embodiments $R^1$ is an unsubstituted alkyl chain.

Most preferably $R^1$ is an optionally-substituted alkyl or alkenyl chain. It may be straight chained or branched. Most preferably it is substantially straight chained and any branching is minimal, for example one or two methyl or ethyl residues may be branched from a long main chain. In especially preferred embodiments $R^1$ is not branched.

Most preferably $R^1$ is an unsubstituted alkyl chain having from 12 to 24 carbon atoms. In especially preferred embodiments R is an unsubstituted straight chain alkyl group having from 16 to 20 carbon atoms.

$R^4$ is preferably an alkylene or alkenylene moiety having from 2 to 36 carbon atoms, preferably from 4 to 30 carbon atoms, for example from 8 to 26 carbon atoms, more preferably from 10 to 20 carbon atoms and most preferably from 12 to 18 carbon atoms.

$R^4$ may be straight chained or may include branching and may optionally include substituents. $R^4$ may be substituted with one or more groups selected from hydroxy, alkoxy (especially methoxy), halo (especially chloro or fluoro), nitro, sulfoxy, alkylsulfoxy, amino, mercapto and trifluoromethyl.

One or more hetero atoms may be incorporated into the chain, for example O, S or N to form an ether, a thioether or an amine. The chain may be alkenyl and thus may include one or more double bonds.

Preferably $R^4$ is an optionally-substituted alkylene or alkenylene group. If $R^4$ is an alkenylene group, it preferably includes at most one double bond for every six carbon atoms, more preferably at most one double bond for every ten carbon atoms. Any double bonds present may have an E or Z configuration. In especially preferred embodiments $R^4$ does not include any double bonds and is an alkylene chain.

Preferably $R^4$ is a substituted alkylene or alkenylene moiety which includes no more than one substituent per four carbon atoms, preferably no more than one substituent for every six carbon atoms, preferably no more than one substituent for every ten carbon atoms, and most preferably no more than one substituent for each sixteen carbon atoms in the chain. In especially preferred embodiments $R^4$ is an unsubstituted alkylene moiety.

$R^4$ may be straight chained or may include some branching. In preferred embodiments, however, $R^4$ is a straight chain alkylene residue having 12 to 18 carbon atoms.

Each of $R^2$ and $R^3$ may be independently selected from an alkylene, alkenylene, alkynylene, arylene, arylalkylene and alkylarylene moiety having from 1 to 30 carbon atoms, preferably 4 to 20, more preferably from 6 to 15 carbon atoms.

Each of $R^2$ and $R^3$ may be straight chained or may include branching and may optionally include substituents. Each may be independently substituted with one or more groups selected from hydroxyl, alkoxy (especially methoxy), halo (especially chloro or fluoro), nitro, sulfoxy, alkylsulfoxy, amino, mercapto and trifluoromethyl.

One or more hetero atoms may be incorporated into either or each chain, for example O, S or N to form an ether, a thioether or an amine. Either or each chain may be alkenylene and thus may include one or more double bonds.

Preferably each of $R^2$ and $R^3$ is an optionally-substituted alkylene or alkenylene group. If either or each is an alkenylene group, it preferably includes at most one double bond for every six carbon atoms, more preferably at most one double bond for every ten carbon atoms. Any double bonds present may have an E or Z configuration. Preferably $R^2$ does not include any double bonds. Preferably $R^3$ does not include any double bonds.

Preferably each of $R^2$ and $R^3$ is an optionally substituted alkylene or alkenylene moiety which includes no more than one substituent per four carbon atoms, preferably no more than one substituent for every six carbon atoms, preferably no more than one substituent for every ten carbon atoms in the chain. Preferably $R^2$ is an unsubstituted alkylene moiety. Preferably $R^3$ is an unsubstituted alkylene moiety.

Most preferably each of $R^2$ and $R^3$ is an alkylene residue which is unsubstituted and straight chained.

P may be hydrogen to provide the free acid, alkyl to provide an ester, a metal, ammonium or phosphonium species, or a sugar residue. Suitable sugar residues include arabinose, trehalose and glucose.

In some preferred embodiments, P is hydrogen.

Each of X, Y and Z may be independently selected from an alkylene group, a cycloalkylene group, a moiety including a ketone, a thioketone or an imine, a moiety including a hydroxyl, thiol or amine moiety, a moiety including an alkoxy residue, a moiety including an epoxide or a moiety including an alkene; with the proviso of course that at least one of X, Y and Z includes a moiety selected from cyclopropyl, C=A, C-AH and C—$OR^5$.

Preferably at least one or X, Y and Z includes a moiety selected from cyclopropyl, C=A and C=AH. More preferably at least one of X, Y and Z includes moiety selected from cyclopropyl and C=A, especially cyclopropyl and C=O.

Suitably each of X, Y and Z contributes a two or three carbon fragment to the main chain. Such a 2 or 3 carbon fragment may suitably include a methyl substituent.

Preferably each of X, Y and Z is independently selected from one or more of the units shown in FIG. B:

FIG. 2

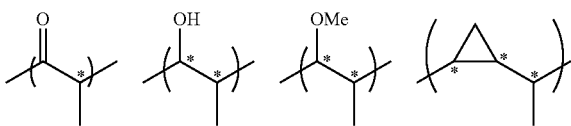

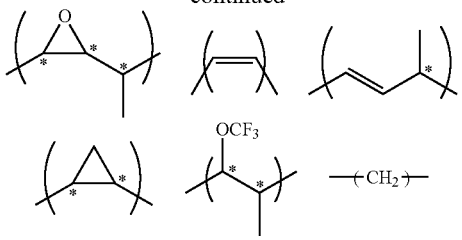

The substituents may be included in either orientation with respect to the mycolic acid motif; hence either regioisomer may be present. Further the unit may include any of the possible stereoisomers resulting from the different chiral centres indicated (*) in FIG. B.

In preferred embodiments Y is $CH_2$ and thus the unit "$R^2$—Y—$R^3$" may be regarded in preferred embodiments as an alkylene chain of formula $(CH_2)_n$. n is preferably from 1 to 40, more preferably from 5 to 30, preferably from 10 to 25, for example from 16 to 22.

In preferred embodiments X includes a cyclopropyl moiety. This group may have a cis or a trans configuration. In some preferred embodiments it has a trans configuration. In some preferred embodiments it has a cis configuration.

In some preferred embodiments X includes a methyl substituent. The carbon carrying the methyl substituent may have an (R) or (S) configuration.

In some embodiments X may include a unit including a cyclopropyl moiety which contributes two carbon atoms to the main chain or a unit including a cyclopropyl moiety and on an adjacent carbon a methyl substituent, which contributes three carbon atoms to the main chain. In such embodiments the methyl substituent may be between the cyclopropyl unit and the mycolic acid motif, that is proximal to the mycolic acid motif, or it may be distal from the mycolic acid motif. Preferably it is distal from the mycolic acid motif. Any relative stereochemistry between the cyclopropane moiety and methyl group may be present. Suitably the α-methyl cyclopropyl unit has (R), (S), (R), or (S), (R), (S) stereochemistry.

In some embodiments X includes an alkene. This may be a cis or trans alkene. It may be di- or trisubstituted. Preferably it is disubstituted. X may include a methyl substituent at a position a to the alkene moiety. Such a methyl substituent may be proximal or distal relative to the mycolic acid functionality.

In some preferred embodiments group Z includes a cyclopropyl group, the moiety C—$OR^5$ or the moiety C=A or C-AH wherein A is O, S or $NR^6$. $R^6$ may be hydrogen or an alkyl group. When $R^6$ is an alkyl group, it is preferably an alkyl group having 1 to 10 carbon atoms, more preferably from 1 to 4 carbon atoms, for example methyl or ethyl.

When Z includes a cyclopropyl unit, two carbons of the cyclopropyl group lie within the long carbon chain. The cyclopropyl group may have a cis or a trans configuration.

When Z includes a cyclopropyl unit, it may include within the long chain a two carbon cyclopropyl unit or a three carbon unit including a cyclopropyl unit and, on an adjacent carbon, a methyl group. Either regioisomer of such an a-Methyl cyclopropyl unit may be present. That is, the methyl group may be proximal or distal relative to the mycolic acid motif. Any relative stereochemistry between the cyclopropyl moiety and methyl group may be present. Suitably the α-methyl cyclopropyl unit has (R), (S), (R) or, preferably (S), (R), (S) stereochemistry.

In some preferred embodiments, Z includes the group C=A or C-AH.

The carbon atom of the group C=A or C-AH lies in the main long chain of the molecule.

In especially preferred embodiments A is O and the group Z includes a carbonyl or alcohol functionality. The preferred carbonyl group is a ketone.

In preferred embodiments Z is a two-carbon fragment which includes an alcohol or especially a ketone and a to this group a methyl substituent.

When Z includes an alcohol, the methyl substituent may have any relative stereochemistry compared with the hydroxyl group and each of the methyl group and hydroxyl group may be (R) or (S) independently. When Z includes an α methyl ketone, the methyl group may have either sterochemistry. This is a readily epimerisable centre and thus a racemic mixture is commonly found. However single stereoisomers can be synthesized and are within the scope of the present invention.

Thus in preferred embodiments Z includes an α-methyl ketone or an α-methyl hydroxy moiety. An α-methyl ketone is especially preferred.

The methyl group may be distal to the mycolic acid motif relative to the ketone/alcohol functionality or it may be proximal. Preferably the methyl group is distal from the mycolic acid motif.

In some preferred embodiments Z includes a moiety C—OR$^5$. The carbon atom lies in the main long chain of the molecule and R$^5$ is an alkyl or haloalkyl group. Hence in some preferred embodiments Z is a group including an alkoxy or haloalkoxy substituent wherein the alkoxy or haloalkoxy group is suitably appended directly to a carbon atom that lies in the main long chain of the molecule.

Preferably R$^5$ is $C_1$ to $C_4$ alkyl or haloalkyl. In some preferred embodiments R$^5$ is $C_1$ to $C_4$ alkyl and may suitably be methyl, ethyl, propyl (including isopropyl and n-propyl) or butyl (including n-butyl, tert-butyl, isobutyl and sec-butyl). Preferred are methyl and ethyl. Most preferably R$^5$ is methyl i.e. Z is a group having a methoxy substituent.

In some embodiments R$^5$ may be $C_1$ to $C_4$ haloalkoxy. A haloalkoxy group includes any alkyl group in which one or more hydrogen atoms has been replaced by a halogen atom, for example bromine, chlorine or fluorine. Preferred haloalkoxy moieties are those including one or more chlorine or, especially fluorine atoms. Suitably all of the hydrogen atoms of an alkyl group have been replaced with halogen atoms in the haloalkoxy group, preferably all have been replaced with fluorine. Especially preferred haloalkoxy groups are pentafluoroethoxy, trifluroethoxy and most preferably trifluoromethoxy.

In some preferred embodiments Z is a two-carbon fragment which includes an alkoxy or haloalkoxy (especially methoxy) substituent and a to this group a methyl substituent.

The methyl substituent may have any relative stereochemistry compared with the alkoxy or haloalkoxy group and each of the carbon atoms bearing the methyl group and the methoxy group may be (R) or (S) independently.

Thus in some preferred embodiments Z includes an α-methyl β-alkoxy moiety, or an α-methyl β-haloalkoxy moiety. An α-methyl β-alkoxy moiety is preferred and an α-methyl β-methoxy moiety is especially preferred.

The methyl group may be distal from the mycolic acid motif relative to the alkoxy or haloalkoxy functionality or it may be proximal. Preferably the methyl is distal from the mycolic acid motif.

In especially preferred embodiments, the present invention provides compounds of formula IIa, IIb, IIc or IId:

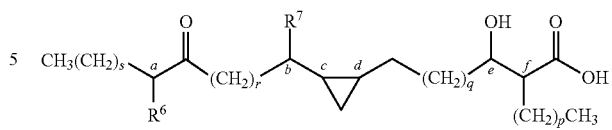

IIa

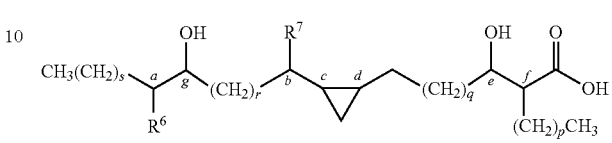

IIb

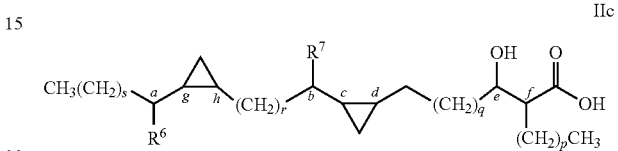

IIc

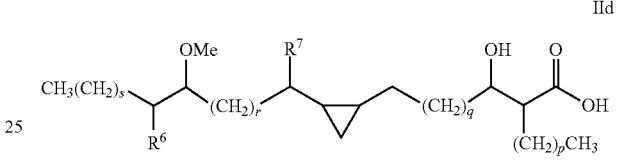

IId for use in the treatment of a disease of the immune system.

In preferred embodiments the present invention provides compounds of formula IIa, IIb or IIc for in the treatment of a disease of the immune system. In especially preferred embodiments the present invention provides compounds of formula IIa or IIc for use in the treatment of a disease of the immune system.

In each of the structures IIa, IIb, IIc and IId R$^6$ may be hydrogen or $C_1$ to $C_4$ alkyl. Preferably R$^6$ is hydrogen or methyl.

In each of the structures IIa, IIb, IIc and IId R$^7$ may be hydrogen or $C_1$ to $C_4$ alkyl. Preferably R$^7$ is hydrogen or methyl.

In each of the structures IIa, IIb, IIc and IId p is preferably from 4 to 40, preferably from 8 to 36, more preferably from 12 to 32, for example from 16 to 30, more preferably from 20 to 28, for example from 22 to 26.

In the structures IIa, IIb, IIc and IId q is preferably from 2 to 40, more preferably from 4 to 36, for example from 6 to 30, preferably from 8 to 24, for example from 10 to 20 and preferably from 12 to 18.

In the structures IIa, IIb, IIc and IId, r is preferably from 2 to 40, for example from 6 to 36, preferably from 10 to 32, for example from 12 to 28, and preferably from 14 to 24.

In the structures IIa, IIb, IIc and IId, s is preferably from 2 to 40, for example from 6 to 36, preferably from 10 to 32, for example from 12 to 28, and preferably from 14 to 24.

In the structures IIa, IIb, IIc and IId, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

The stereocentre indicated at position a may have an (R) or an (S) configuration.

The stereocentre at b may have an (R) or an (S) configuration.

The stereocentre at c may have an (R) or an (S) configuration.

The stereocentre at d may have an (R) or an (S) configuration.

The stereocentre at e may have an (R) or an (S) configuration.

The stereocentre at f may have an (R) or an (S) configuration.

The stereocentre at g may have an (R) or an (S) configuration.

The stereocentre at h may have an (R) or an (S) configuration.

The present invention relates to the treatment of diseases of the immune system, in particular the immune system of mammals and especially humans.

Suitably the disease treated is a disease involving an out of control immune response or pathology causing immune response, for example an allergic immune disease or an autoimmune disease.

Preferably the compounds of the present invention are useful in the treatment of a disease in which Th2-lymphocyte activity contributes to the immune disease.

Examples of diseases which may be treated according to the present invention include asthma, rhinitis, hay fever, eczema and other allergic diseases; and autoimmune diseases, for example, systemic lupus erythematosus, Goodpasture's syndrome, Grave's disease, Myasthenia Gravis, type I diabetes and multiple sclerosis.

In preferred embodiments, the present invention is useful in the treatment of asthma and other allergic diseases. Allergic diseases are known to the person skilled in the art and include, but are not limited to, allergic asthma, allergic rhinitis, allergic conjunctivitis, eczema, airway hyperactivity, eosinophilic airway inflammation and atopic dermititis.

The present inventors have observed that in animal studies some compounds of formula I may cause foaming of macrophages. Without wishing to be bound by any theory, it is believed that when compounds of formula I are taken up by antigen-presenting cells foaming occurs. These foaming cells have suppressive effects within the immune system. It is believed that when the foamed cells are induced by compounds of formula I, they activate regulatory T cells which suppress the Th2 immune response.

Especially preferred compounds of formula I are those which have little or no inflammatory effects. Compounds of formula I in which P is hydrogen have low inflammatory effects.

In particular compounds having the structures shown in figures IIa, IIb and IIc have been found to have low inflammatory effects. The inflammatory effects of these compounds prepared as single compounds have been found to be lower than for natural mixtures of mycolic acids.

According to a second aspect of the present invention there is provided compounds of formula I except for compounds of formula III:

III

-continued

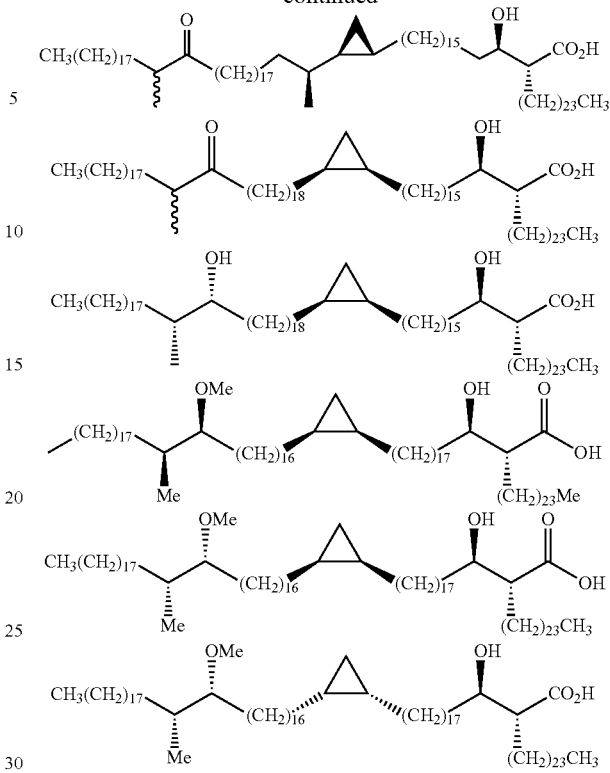

Compound I is as defined in relation to the first aspect and preferred features of the first aspect apply equally to the second aspect.

The compounds of the second aspect are suitably available in highly purified forms, preferably as single homologues and preferably single regioisomers and single stereoisomers. Suitable they are at least 90% pure, preferably at least 95% pure, for example at least 98% or 99% pure.

The compounds of the present invention may be prepared by any suitable means. They may be extracted from natural sources and optionally purified. They may be prepared by biosynthetic methods or they may be prepared synthetically.

Preferably the compounds of the present invention are prepared synthetically. An advantage of using compounds which are prepared synthetically is that single compounds can be prepared in very high purity having a single stereochemistry. A disadvantage of compounds isolated from natural sources for example, is that mixtures are often obtained, including different isomers and/or different classes of mycolic acids and/or in particular different homologues. Although these other compounds may sometimes only be present in trace amounts, for pharmaceutical use synthetic compounds not containing other stereoisomers or homologues is highly desirable. It is possible that mixtures of synthetic compounds may be used in the present invention. However the exact composition of such mixtures may be carefully controlled to include known amounts of individual components which have been prepared separately and characterised.

Suitable methods for preparing compounds for use in the present invention are described in previous publications of the inventors. See for example Al Dulayymi J R, Baird M S and Roberts E, Chem Commun (Camb) 2003:228-9; Al Dulayymi J R, Baird M S and Roberts E., Tetrahedron 2005; 61:11939-11951; Al Dulayymi J R, Baird M S, Roberts E, Deysel M and Verschoor J., Tetrahedron 2007; 63:2571-2592; Al Dulayymi J R, Baird M S, Roberts E and Minnikin D E., Tetrahedron 2006; 62:11867-11880; Al-Dulayymi J R, Baird M S, Mohammed H, Roberts E and Clegg W., Tetrahedron 2006; 62:4851-4862; Koza G, Baird M S., Tetrahedron Letters 2007; 48:2165-2169; and Toschi G, Baird M S., Tetrahedron 2006; 62:3221-3227.

According to a third aspect of the present invention there is provided a composition comprising a mixture of two or more compounds of formula I.

Such mixtures may include in addition to quite structurally different compounds, mixtures of different stereo and regioisomers, as well as different homologues. However an advantage of such mixtures of the present invention is that controlled mixtures including specific amounts of well defined components can be prepared unlike mixtures of the prior art obtained from natural sources. These natural mixtures may contain unknown or variable amounts of the various components as well as possibly unidentified components.

According to a fourth aspect of the present invention there is provided a composition comprising a compound of formula I and a pharmaceutically-acceptable carrier.

Any suitable pharmaceutically-acceptable carrier may be used and is suitably selected from those known to the person skilled in the art.

The pharmaceutically-acceptable carrier may be a solid, for example polymer dust or a sugar; a micelle, for example a liposome; a liquid, for example a water-in-oil emulsion, or a solution, typically a saline solution or phosphate buffered saline; a gas; or a transdermal delivery system. When the carrier is a liquid, the composition may be in the form of a suspension or a vaporised liquid, typically a nebulisable physiological saline solution.

The compounds of the present invention are particularly effective in the treatment of asthma and thus preferred carriers are selected to achieve this purpose.

The compounds of the present invention are suitably delivered in combination with a carrier that is compatible with hydrophobic compounds.

It is particularly advantageous to deliver the compounds of the present invention in combination with a liposome.

The composition of the fourth aspect may include a single compound of formula I or it may include a mixture of two or more compounds of formula I as defined in relation to the third aspect.

In some embodiments the composition of the third aspect or the composition of the fourth aspect of the present invention may include further mycolic acid-derived compounds in addition to those of formula I. Preferably however, of mycolic acid-derived compounds present in the composition of the third or fourth aspects of the present invention, at least 50 wt % are compounds of formula I, more preferably at least 80 wt %, preferably at least 90 wt %, more preferably at least 95 wt %, most preferably at least 99 wt %.

In some embodiments, two or more compounds of formula I from the same or different mycolic acid subclass may be combined in a synergistic formulation. For example, a combination of an α-mycolic acid (where Z includes a cyclopropyl unit) and a keto-mycolic acid (where Z includes a C=O moiety) may be used.

In some embodiments however, addition of one or more compounds from a different subclass of mycolic acids may act synergistically with compounds of formula I to provide therapeutic benefits.

The composition of the third aspect may further comprise one or more active ingredients, for example those selected from small amounts of bronchodilators, for example sympathomimetic amines such as isoprenaline, isoetharine, salbutamol, phenylephrine and ephedrine; xanthine derivatives such as theophylline and aminophylline; corticosteroids such as prednisolone; and adrenal stimulants such as ACTH.

The composition of the fourth aspect may further comprise one or more optional excipients, for example colourants, flavourings, fillers, antioxidants, stabilisers and taste-masking agents.

The form of the composition of the fourth aspect of the present invention will depend on the method by which it is intended to be administered. The composition of the fourth aspect may be formulated to enable it to be administered in any suitable form.

The composition may be provided in solid ingestible form, for example as a pill or capsule. One such possible formulation is a polymeric capsule the surface or lumen of which carries compounds of formula I. It may be provided in a liquid ingestible form, for example as a syrup or elixir.

In some embodiments there may be provided a kit comprising a composition comprising a compound of formula I and a composition comprising a carrier. These two compositions may suitably be combined prior to use. This may be useful if, for example, the dosage form is not stable to long periods of storage.

In preferred embodiments the composition is in a form suitable for administration to a sufferer of asthma. This may comprise a solid or liquid ingestible form as described above or it may be provided in a form suitable for topical administration. For example the composition may be provided as a liquid which can be delivered nasally or as a dry powder, suspension or solution which can be inhaled.

Preferably, compositions for inhalation are presented for administration to the respiratory tract as a snuff or an aerosol or solution for a nebulizer, or as a microfine powder for insufflation, alone or in combination with an inert carrier, for example lactose. In such a case the particles of active compound suitably have diameters of less than 50 microns, preferably less than 10 microns, for example between 1 and 5 microns, such as between 2 and 5 microns.

Although the present invention relates primarily to the treatment of diseases of the immune system of humans, it may also be used to treat diseases of the immune system of other mammals, for example, allergic diseases such as skin diseases.

According to a fifth aspect of the present invention there is provided a method of treating a mammal having a disease of the immune system by administering to said mammal a compound of formula I.

Preferred features of the fifth aspect are as defined in relation to the first, second, third and fourth aspects.

In the method of the fifth aspect, the compound of formula I may be administered by any suitable means. It is suitably administered in the form of a composition of the fourth aspect.

The compounds of the present invention may be administered via inhalation, intravenously, orally, subcutaneously, by intramuscular injection, by suppository or enema form, intranasally, by topical application, buccally, sublingually or transdermally.

Preferably the compounds are administered in a non-invasive manner, most preferably by inhalation.

The method of treatment of the present invention may be curative or it may be prophylactic. For example in the treatment of asthma, dosing of the compounds of the present invention in advance may prevent a user from suffering an allergic asthmatic reaction upon subsequent exposure to an allergen.

In some embodiments it may be preferable to administer compounds of formula I in combination with a known antigen. Such antigens are suitably those known to be involved in an allergic disease or autoimmune disease.

In some embodiments, a subject is first treated with a compound of formula I and after a suitable period is exposed to an antigen. Exposure to an antigen may occur naturally from the environment, from within the body itself or there may be controlled exposure to an antigen.

Preferably the compound of formula I is administered in the form of a unit-dose composition, such as a unit dose nasal or inhaled composition. The formulation of a suitable unit dose is within the competence of the person skilled in the art. The amount of compound delivered in a unit dose will depend on the efficacy of the particular compound, the delivery method, the intended recipient and the delivery regime. For example in some cases a smaller unit dose may be delivered more frequently than a larger unit dose and the unit dose for a child will typically be lower than for an adult.

Dependent on the form of the unit-dose composition, devices suited for delivery typically are pressurized aerosols, nebulisers and dry powder inhalers designed for efficient and reproducible delivery, flexible dosing and allowing for patient control on intake of the composition.

The present invention will now be further described with reference to the following non-limiting examples.

EXAMPLES

Animals

Female C57Bl/6N mice were purchased from Janvier and housed under specific pathogen free conditions in individually ventilated cages and fed ad libitum. Mice were 8-12 weeks old at the start of experiments.

Example 1

Natural Mycolic Acid Compounds

The natural mycolic acid compounds used in the comparative examples were obtained from Sigma and comprise a crude isolate from the cell wall of M. tuberculosis H37Rv. This mixture is referred to in the examples as "crude-MA".

Example 2

Synthesis of Model Mycolic Acid

A model synthetic compound containing the mycolic acid motif as a mixture of stereoisomers and a meromycolic chain free of functional moieties served as a control mycolate. It was obtained by condensation of two methyl behenate molecules with sodium methoxide, followed by reduction of the derived methyl ester of the corresponding keto-acid and ester hydrolysis. This comparative example is referred to as compound 1 and the structure thereof is shown in table 1.

Example 3

Preparation of Single Isomer of Keto-mycolic Acid of Formula

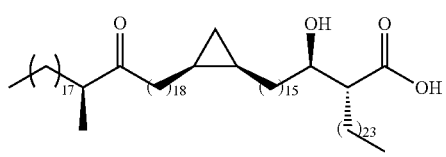

The compound having the structure above was prepared according to the following procedure. After each stage the structure of the product was fully characterised by NMR spectroscopy, IR, mass spectroscopy and the optical rotation was recorded.

Example 3a (8S,9S)-9-methyl-1-(tetrahydropyran-2-yloxy)-heptacosan-8-ol was prepared according to the method published by J. R. Al Dulayymi, M. S. Baird, E. Roberts, M. Deysel and J. Verschoor; Tetrahedron 63 (2007); 2571-2592. This material was protected as the tert-butyl dimethyl silyl ether by treatment with tert-butyl-dimethylsilylchloride and imidazole in DMF at room temperature. The product was then treated with Pyridinium-p-toluenesulfonate to give (8S,9S)-8-(tert-butyldimethylsilanyloxy)-9-methylheptacosan-1-ol. in (94% yield). The alcohol was oxidised using PCC to give (8S,9S)-8-(tert-butyldimethylsilanyloxy)-9-methylheptacosanal in 97% yield.

Example 3b 2,2-dimethyl-propionic acid 10-bromodecyl ester was prepared in 85% yield by treatment of 10-bromodecan-1-ol with trimethylacetyl chloride in the presence of pyridine and 4-dimethylaminopyridine at room temperature in dithlcromethane. After 18 hrs, the reaction was quenched by the addition of dilute hydrochloric acid worked up and filtered through silica to provide 2,2-dimethyl-propionic acid 10-bromodecyl ester.

The ester was treated with 1-Phenyl-1H-tetrazole-5-thiol and two equivalents of anhydrous potassium carbonate in acetone at room temperature for 18 hrs. Chromatography provided 2,2-dimethylpropionic acid 10-(1-phenyl-1H-tetrazol-5-ylsulfan-yl)decyl ester in 93% yield.

This compound was reacted with a solution of ammonium molybdate (VI) tetrahydrate in 35% $H_2O_2$ to provide 2,2-dimethylpropionic acid 10-(1-phenyl-1H-tetrazole-5-sulfonyl)decyl ester in 97% yield.

Example 3c

A THF solution comprising the compound prepared in example 3a and the compound prepared in example 3b was cooled to −10° C. and treated with lithium bis(trimethylsilyl) amide. After stirring at room temperature for 1.5 hrs the reaction worked up to provide 2,2-dimethylpropionic acid (E/Z)-(18S,19S)-18-(tert-butyldimethylsilanyloxy)-19-methylhepta-triacont-10-enyl ester as a mixture of two isomers. These were reduced by hydrogenation using 10% palladium on carbon as a catalyst in ethanol and ethyl acetate.

The resultant ester was reduced using lithium aluminium hydride to provide (18S,19S)-18-(tert-butyldimethylsilanyloxy)-19-methylhepta-triacontan-1-ol as a colourless oil in 95% yield. The alcohol was then oxidised using PCC to give (18S,19S)-18-(tert-butyldimethylsilanyloxy)-19-methylheptatriacontanal in 95% yield.

Example 3d

The aldehyde obtained in example 3c was added to a stirred solution of butyric acid (1R,2S)-2-(1-phenyl-1H-tetrazole-5-sulfonylmethyl)-cyclopropylmethyl ester and treated with lithium bis(trimethylsilyl) amide at −5° C. Stirring at room temperature for 1½ hrs and workup provided butyric acid (1R,2S)-2-[(E/Z)-(19S,20S)-19-(tert-butyldimethylsilanyloxy)-20-methyloctatriacont-1-enyl]-cyclopropyl methyl ester as a mixture of two isomers in a ratio of 2.5:1. This was reacted with 2,4,6-tri-isopropylbenzenesulphonyl hydrazide THF at 40° C. for 27 hrs. The reaction mixture was worked up and purified as above to give, butyric acid (1R,2S)-2-[(19S, 20S)-19-(tert-butyl-dimethyl-silanyloxy)-20-methyl-octatriacontyl]cyclopropyl methyl ester in 76% yield. This compound was reduced to the alcohol using lithium aluminium hydride and then oxidised with PCC to give (1R,2S)-2-[(19S, 20S)-19-(tert-butyldimethyl-silanyloxy)-20-methyloctatriacontyl]cyclopropanecarbaldehyde in 96% yield.

Example 3e

Acetic acid (R)-1-(2-benzyloxyethyl)-but-3-enyl ester was prepared from (S)-1-benzyl-oxyhex-5-en-3-ol by treatment with acetic anhydride and pyridine in toluene. This ester was treated with oxone and then $OsO_4$ to give (R)-3-acetoxy-5-benzyloxypentanoic acid in 78% yield. The acid was then refluxed in methanol under acidic conditions to provide the methyl ester Following deprotonation with lithium diisopropylamide, the methyl ester was treated with allyl iodide in the presence of HMPA. The product was purified by chromatography to provide (R)-2-((R)-3-benzyloxy-1-hydroxypropyl)pent-4-enoic acid methyl ester in 76% yield.

Example 3f

The compound obtained in example 3e was protected as the tert-butyl dimethyl silyl ether by treatment with tert-butyldimethylchlorosilane and imidazole in DMF. This compound was treated with 2,6-lutidine and $OsO_4$ 2.5% in 2-methyl-2-propanol, followed by $NaIO_4$ in 1,4-dioxane-water (3:1) at room temperature. The reaction was stirred at 25° C. for 2 hrs, quenched, and the product purified by chromatography to provide (2R,3R)-5-benzyloxy-3-(tert-butyldimethylsilanyloxy)-2-(2-oxoethyl)pentanoic acid methyl ester in 88% yield.

Example 3g

Lithium bis(trimethylsilyl)amide was added to a stirred solution of the compound formed in example 3f and 5-(docosane-1-sulfonyl)-1-phenyl-1H-tetrazole in THF. After stirring at room temperature for 3 hrs, the reaction was quenched and worked up to give (E/Z)-(R)-2-[(R)-3-benzyloxy-1-(tert-butyl-dimethylsilanyloxy)-propyl]hexacos-4-enoic acid methyl ester (6.43 g, 83%) as a mixture of two isomers in ratio 2:1. Hydrogenation in the presence of palladium 10% on in THF/IMS afforded (R)-2-[(R)-3-benzyloxy-1-(tert-butyldimethylsilanyloxy) propyl]hexacosanoic acid methyl ester in 98% yield.

Hydrogenation for 3 days in the presence of palladium 10% on carbon in ethyl acetate effected deprotection of the benzyl group in 95% yield. The resultant alcohol was then oxidised using PCC to provide (R)-2-[(R)-1-(tert-butyldimethylsilanyloxy)-3-oxopropyl]hexacosanoic acid methyl ester in 90% yield.

Example 3h

1-Phenyl-1H-tetrazole-5-thiol, 12-bromododecan-1-ol and anhydrous potassium carbonate were mixed together in acetone for 18 hrs at room temperature to provide 12-(1-phenyl-1H-tetrazol-5-ylsulfanyl)-dodecan-1-ol in 77% yield following work up and recrystallisation. Ammonium molybdate (VI) tetrahydrate in 35% $H_2O_2$ were added to a stirred solution of the solid in THF IMS (500 ml) at 10° C. and stirred at room temperature for 20 hrs. Work-up and crystallisation gave a white solid (m.p.: 56-58° C.), 12-(1-phenyl-1H-tetrazol-5-sulfonyl)-dodecan-1-ol in 95% yield. N-Bromosuccinimide was added to a solution of the alcohol and triphenylphosphine in dichloromethane and the reaction stirred at room temperature for 75 min. Work-up and purification by chromatography provided a white solid (m.p.: 63-65° C.), 5-(12-bromo-dodecane-1-sulfonyl)-1-phenyl-1H-tetrazole in 72% yield.

Example 3i

Lithium bis(trimethylsilyl)amide was added to a stirred THF solution of the compound prepared in example 3g and the compound prepared in example 3h. The reaction was stirred at room temperature for 3 hrs, quenched and purified by chromatography to provide (R)-2-[(E/Z)-(R)-15-bromo-1-(tert-butyldimethylsilanyloxy)penta-dec-3-enyl]hexacosanoic acid methyl ester (4.19 g, 82%) as a 2:1 mixture of two isomers. Hydrogenation in the presence of palladium 10% on carbon in THF and ethanol (1:1) gave (R)-2-[(R)-15-bromo-1-(tert-butyldimethylsilanyloxy)pentadec-yl]hexacosanoic acid methyl ester in 92% yield after 3 hours.

Example 3j

The compound prepared according to example 3i was stirred with 1-phenyl-1H-tetrazole-5-thiol and anhydrous potassium carbonate in acetone for 18 hrs at room temperature. Work-up and chromatography gave (R)-2-[(R)-1-(tert-butyldimethylsilanyloxy)-15-(5-phenyl-5H-tetrazol-1-ylsulfanyl)pentadecyl]hexacosanoic acid methyl ester in 86% yield.

The tert-butyldimethylsilyl protecting group was removed by stirring with HF and pyridine in THF in 84% yield and the resultant alcohol was reprotected as the acetate by treatment with acetic anhydride and anhydrous pyridine to give (R)-2-[(R)-1-acetoxy-15-(5-phenyl-5H-tetrazol-1-ylsulfanyl)pentadecyl]hexacosanoic acid methyl ester in 83% yield.

This compound was treated with m-Chloroperbenzoic acid and $NaHCO_3$ in dichloromethane (40 ml) and stirred at room temperature for 20 hrs. Work-up and chromatography afforded a white solid, (R)-2-[(R)-1-acetoxy-15-(5-phenyl-5H-tetrazol-1-sulfonyl)pentadecyl]hexacosanoic acid methyl ester in 82% yield.

Example 3k

The ester obtained in example 3j was dissolved in dry THF along with (1R,2S)-2-[(19S,20S)-19-(tert-butyldimethylsilanyloxy)-20-methyloctatriacontyl]cyclopropane carbaldehyde and lithium bis(trimethylsilyl) amide was added. The solution was stirred at room temperature for 2 hrs, before being worked up and purified by chromatography to give (R)-2-((R)-1-acetoxy-16-{(1R,2S)-2-[(19S,20S)-19-(tert-butyld ethylsilanyloxy)-20-methyl-octatriacontyl]cyclopropyl}hexadec-15-enyl)hexacosanoic acid methyl ester in 72% yield as a 4:1 mixture of two isomers.

Dipotassium azodicarboxylate was added to a stirred solution of the alkenes in THF and methanol (5:1) at 5° C. A solution of glacial acetic acid) and THF (2 ml) was added and the mixture was stirred for 48 hours. Work up and chromatography provided (R)-2-((R)-1-acetoxy-18-{(1R,2S)-2-

[(19S,20S)-19-(tert-butyldimethyl-silanyloxy)-20-methyloctatriacontyl]cyclo propyl} octadecyl)-hexacosanoic acid methyl ester in 91% yield.

Example 3l

Removal of the tert-butyldimethylsilyl protecting group from the compound obtained in example 3k was achieved by treatment with HF and pyridine to provide (R)-2-((R)-1-acetoxy-16-{(1R,2S)-2-[(19S,20S)-19-hydroxy-20-methyloctatriacontyl]cyclopropyl}-octadecyl) hexacosanoic acid methyl ester in 73% yield after chromatography.

Treatment of the resultant alcohol with pyridinium p-toluene sulphonate and dihydro-2H-pyran added a THP protecting group 86% yield.

Hydrolysis of the ester was achieved by addition of lithium hydroxide monohydrate to a stirred solution of the ester in THF, methanol and water at room temperature. The mixture was stirred at 45° C. for 16 hrs, worked up and purified by chromatography to give (R)-2-((R)-1-hydroxy-16-{(1R,2S)-2-[(19S,20S)-20-methyl-19-(tetrahydropyran-2-yloxy)octatriacontyl] cyclopropyl}hexadecyl)hexacosanoic acid as a mixture of diastereoisomers in 60% yield.

Example 3m

The compound prepared in example 3l was protected as the tert-butyl-dimethylsilyl ester by treatement with tert-butyl-dimethylsilyl chloride and 4-dimethylaminopyridine. The product was purified by chromatography to give (R)-2-((R)-1-(tert-butyldimethylsilanyloxy)-16-{(1R,2S)-2-[(19S, 20S)-20-methyl-19-(tetrahydropyran-2-yloxy)octatria-contyl]-cyclopropyl}hexa decyl)hexacosanoic acid as a mixture of diastereoisomers in 76% yield.

(Pyridinium-p-toluenesulfonate (100 mg, 0.40 mmol) was added to the above acid (100 mg, 0.07 mmol) in THF (4 ml), MeOH (0.5 ml) and $H_2O$ (0.2 ml) and stirred at 47° C. for 7 hrs. Sat.aq. sodium bicarbonate (3 drops) was added and the product was extracted with petrol/ethyl acetate (3×15 ml, 1:1). The combined organic layers were dried and evaporated. Chromatography eluting with 10:1 petrol/ethyl acetate gave (R)-2-{(R)-1-(tert-butyl-dimethylsilanyloxy)-16-[(1R,2S)-2-((19S,20S)-19-hydroxy-20-methyloctatriacontyl)-cyclopropyl]hexa-decyl}hexacosanoic acid as a white semi-solid (60 mg, 0.044 mmol, 60%), $[\alpha]_D^{25}$ −2.06 (c 0.68, $CHCl_3$).

This compound was treated with PCC in dichloromethane at room temperature for 2 hrs. After work up and chromatography (R)-2-{(R)-1-(tert-butyldimethylsilanyloxy)-16-[(1R, 2S)-2-((S)-20-methyl-19-oxo-octatriacontyl)cyclopropyl] hexa-decyl}hexacosanoic acid was obtained as a white semi-solid in 74% yield.

The final TBDMS deprotection was effected by treatment with hydrogen fluoride and pyridine in THF. Chromatography gave a white solid, (R)-2-{(R)-1-hydroxy-16-[(1R,2S)-2-((S)-20-methyl-19-oxo-octatriacontyl)cyclopropyl] hexadecyl}hexacosanoic acid in 83% yield. $[\alpha]_D^{26}$ +7.34 (c=0.79, $CHCl_3$), m.p. 66-68° C. {Found (M+Na)$^+$: 1260.2522, $C_{84}H_{164}NaO_4$ requires: 1260.2568}. This showed; $\delta_H$: 3.72 (1H, br., pent, J 4.7 Hz), 2.52 (1H, q, J 6.6 Hz), 2.48 (1H, m), 2.42 (2H, dt, J 1.85, 7.25 Hz), 1.78-1.70 (1H, m), 1.67-1.60 (2H, m), 1.59-1.46 (6H, m), 1.4-1.10 (137H, m), 1.05 (3H, d, J 6.95 Hz), 0.89 (6H, t, J 7.25 Hz), 0.71-0.62 (2H, m), 0.56 (1H, br. dt, J 4.1, 8.5 Hz), −0.33 (1H, br. q, J 5.00 Hz); $\delta_C$: 215.42, 179.80, 72.12, 50.86, 46.33, 41.15, 35.51, 33.04, 31.92, 30.23, 29.71, 29.66, 29.52, 29.50, 29.47, 29.43, 29.37, 29.33, 28.73, 27.33, 25.73, 23.73, 22.69, 16.35, 15.78, 14.11, 10.91, $v_{max}$: 3284, 2919, 2850, 1708, 1465, 1377, 721 $cm^{-1}$.

Example 4

Preparation of Other Synthetic Mycolic Acids as Single Compounds

Stereochemically defined synthetic mycolic acid molecules were prepared by analogous methods to that described in relation to example 3 and by methods described in the inventor's previously published papers, the details of which are given above. An (R),(R)-stereoisomer at the hydroxy acid group was prepared using a Frater type alkylation of a R-3-hydroxy-acid. The absolute stereochemistries of cis-cyclopropane and α-methyl-trans-cyclopropane units were defined by starting from an enzyme induced desymmetrisation of cis-cyclopropane-1,2-diol or a derivative, or by asymmetric cyclopropanation of alkenes derived from mannitol or dihydroascorbic acid. The methoxymethyl subunit of $^s$methoxy-MA and the α-methyl-keto group of $^s$keto-MA were introduced in a stereocontolled manner by ring opening of a chiral epoxide.

Some of the synthetic compounds prepared are shown in table 1:

| Compound number | Structure: |
|---|---|
| 4 | 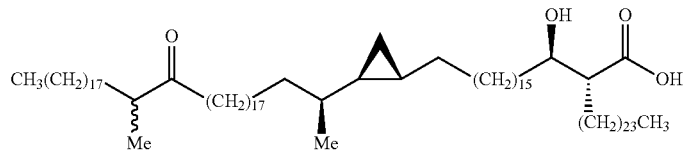 |
| 5 | 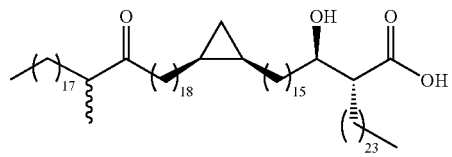 |
| 6 | 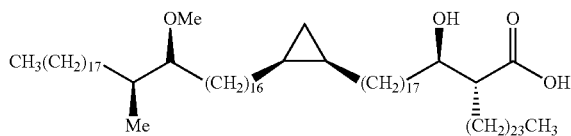 |
| 7 |  |
| 8 | 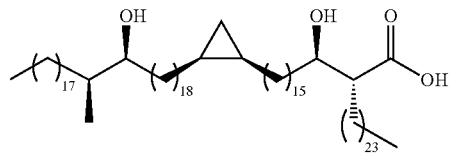 |
| 9 |  |
| 10 | 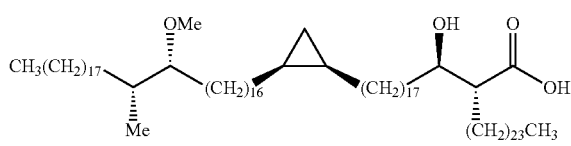 |
| 11 | 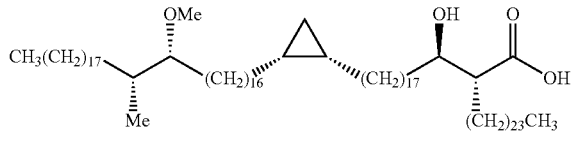 |
| 12 | 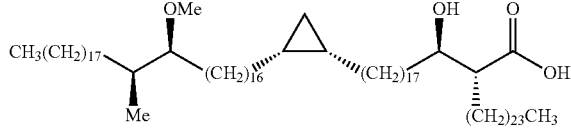 |

-continued

| Compound number | Structure: |
|---|---|
| 13 | |
| 14 | |
| 15 | |
| 16 | |
| 17 | |
| 18 | |
| 19 | |
| 20 | |
| 21 | |
| 22 | |

-continued

| Compound number | Structure: |
|---|---|
| 23 | CH₃(CH₂)₁₇—CH=CH—(CH₂)₁₇—CH(OH)—CH((CH₂)₂₁CH₃)—C(=O)OH |
| 24 | CH₃(CH₂)₁₅—CH(—O—)CH—(CH₂)₁₂—CH=CH—(CH₂)₁₉—CH(OH)—CH((CH₂)₂₁CH₃)—C(=O)OH |
| 25 | CH₃(CH₂)₁₅—CH(—O—)CH—(CH₂)₁₂—CH=CH—(CH₂)₁₉—CH(OH)—CH((CH₂)₂₁CH₃)—C(=O)OH |

Example 5

Preparation of Mycolic Acid Containing Liposomes and In Vivo Administration

Each of the compounds 1 to 9 listed in table 1 and the natural mycolic acid mixture obtained from Sigma (hereinafter crude-MA) were incorporated into liposomes using the method described in Korf J, Stoltz A, Verschoor J, De Baetselier P and Grooten J., Eur J Immunol 2005; 35:890-900. Briefly, the compounds were mixed with phosphatidylcholine (Sigma) in chloroform. The chloroform was evaporated and the lipids recovered in sterile saline. After ultrasound sonication and vortexing, samples of 25 μg mycolic acids/100 μl/mouse were administered intratracheally. A liposome control was prepared similarly, but without the addition of any mycolic acid compound.

Example 6

Foaming of Mycolic Acid Treated Alveolar Macrophages

Formation of cholesterol-rich foamy alveolar macrophages upon intratracheal instillation of mycolic acid containing liposomes is indicative of a possible mycolic acid induced suppression of Th2-mediated eosinophilia. In a mouse model of allergic asthma this is mediated by a mechanism involving antigen presentation by these foam cells and the activity of regulatory T-lymphocytes (Korf et al, Am. J. Respir. Crit. Care Med., 174, 1-9, 2006).

We verified the induction of cholesterol-loaded cells in the lungs of C57BL/6 mice that received a single dose of liposomes carrying compounds a week earlier. The mice were treated with empty liposomes, liposomes containing control compound 1, liposomes containing compound 2 and liposomes containing compound 4. Frozen lung sections were stained with the lipophilic Oil Red O dye (ORO) thereby visualising foam cell intracellular lipid vesicles and counter-stained with haematoxylin. FIG. 1a shows a light microscopy image of an ORO-stained lung section of a mouse treated with compound 4. With the higher magnification of reference panel R shown in FIG. 1b, individual ORO-stained lipid vescicles are visible within the foam cells, as indicated by the arrows.

Figure 2:
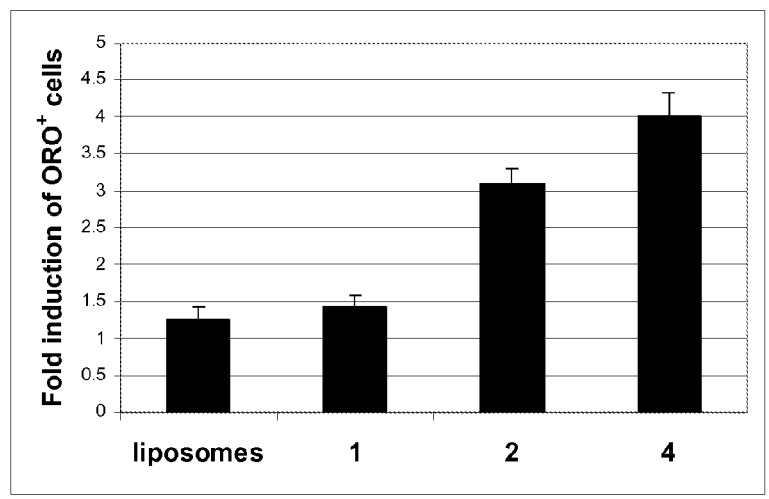
FIG. 2 depicts a histological graph of an analysis of Oil Red O dye (ORO) stained sections of lung using a double-blinded counting set up.

Histological analysis of the ORO-stained sections was carried out using a double-blinded counting set up. The results illustrated in FIG. 2 show that significantly higher scores of ORO positive cells/microscopic field were observed for the liposomes containing compound 2 or compound 4 than for the empty liposomes or those containing compound 1.

These data show that highly pure synthetic single mycolic acid isomers 2 and 4 elicited foam cell accumulation in the lung, which is known to correlate with a beneficial effect on allergic airway responses.

Example 7

Assessment of Inflammatory Cell Infiltration to the Airways and Lung Tissue Damage In order to be considered safe for therapeutic administration, compounds should preferably cause as little local inflammation or resulting tissue changes as possible.

Inflammatory effects were examined by intratracheally administering to C547BL/6 mice empty liposomes, liposomes carrying the comparative natural sample crude-MA and liposomes carrying the synthetic mycolic acid molecules 3, 4 or 9.

Figure 3:
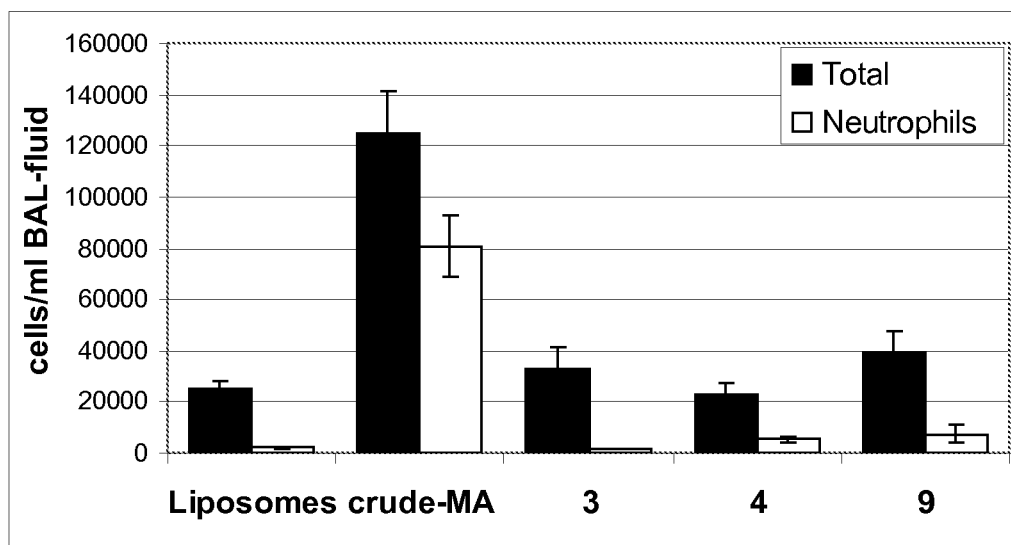
FIG. 3 shows a histological graph of an analysis of total cell and neutrophil count of the broncho-alveolar lavage (BAL) obtained from test mice.

After 48 hours, mice were sacrificed and a broncho-alveolar lavage (BAL) was performed to measure the airway cell types and numbers by flowcytometry. Increased cell numbers and the appearance of granulocytes (mainly neutrophils) in the BAL-fluid are indicative for cell recruitment to the airways as result of an inflammatory reaction. The total cell and neutrophil count of the BAL-fluid is shown in FIG. 3.

Figure 4:
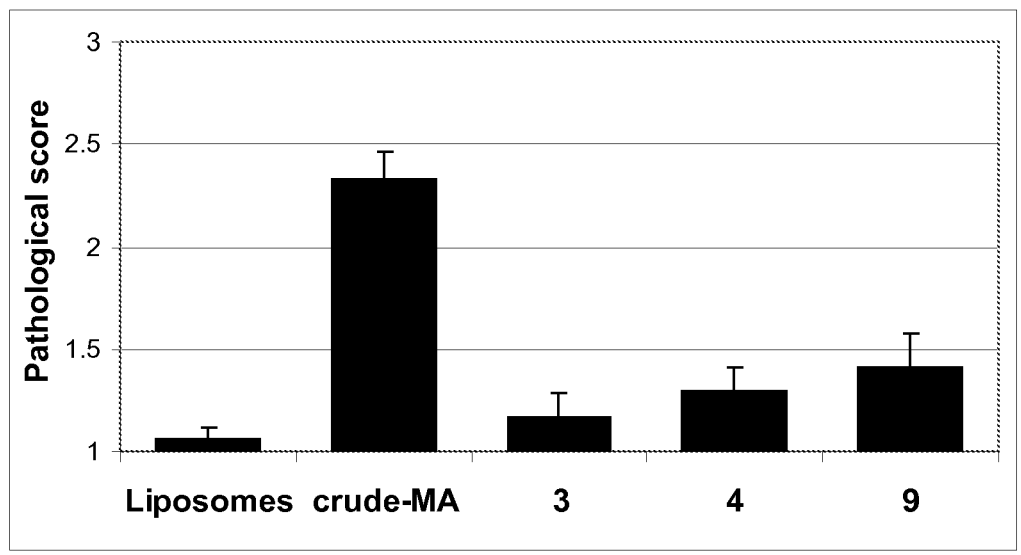
FIG. 4 depicts a histological graph of an analysis based on an analysis of lavaged lungs obtained from test mice.

Lavaged lungs were ectomised to allow for histo-pathological examination of the lung tissue. A haematoxylin and eosin staining of the paraffin lung sections was followed by a thorough examination by a skilled pathologist who scored the sections according to the following criteria in a double-blinded manner:

0=no inflammation
1=a minority of the bronchi are surrounded by some infiltrated inflammatory cells
2=the majority of the bronchi are surrounded by some infiltrated inflammatory cells
3=dispersed are some heavy infiltrates of neutrophils and eosinophils
4=a lot of infiltrating neutrophils and eosinophils throughout the entire lung section
5=same as 4 with additionally signs of airway remodelling e.g. basal membrane thickening, mucus overproduction and/or smooth muscle cell hyperplasia The results are shown in FIG. 4 and indicate that the commercial comparative sample induces significant inflammatory cell infiltration to the airways as compared to empty liposome treatment, whereas liposomes containing molecules 3, 4 and 9 do not. Additionally, compounds 3, 4 and 9 did not cause any significant lung tissue changes in contrast to the crude-MA comparative sample. These results suggest that use of the synthetic mycolic acid compounds 3, 4 and 9 is safe as the vulnerable mouse lungs are not reacting with inflammation upon administration of these compounds. This would suggest that topical application of these molecules in therapy would be unlikely to cause discomfort to the patient.

Example 8

Suppression of Allergic Airway Inflammation in a Mouse Asthma Model

Liposome containing synthetic mycolic acids compounds 5, 6 and 7 were administered intratracheally to mice which had been immunised for the experimental allergen chicken egg ovalbumin (OVA) adjuvanted with Alum (aluminium hydroxide). Following 7 days, the mice were challenged with OVA-aerosol. Th2-driven allergic airway inflammation was apparent in empty liposomes treated animals, from high eosinophil counts in the BAL-fluid by flowcytometry (CCR3+). On the other hand, mice treated intratracheally with liposomes carrying the synthetic molecules 5, 6 or 7 were partially protected against this allergic inflammatory response, as the eosinophil count was at least two-fold decreased.

Figure 5:
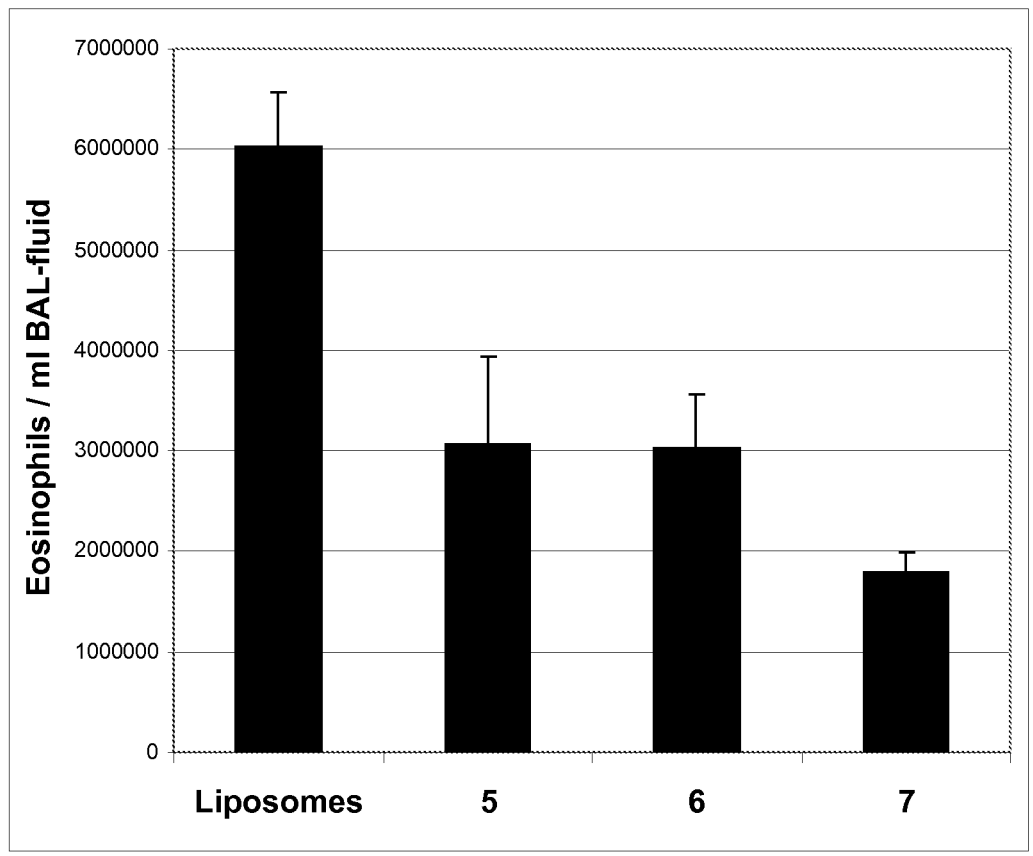
FIG. 5 shows a histological graph of an analysis of the suppression of allergic responses of mice by the administration of synthetic mycolic acids.

The results are shown in FIG. 5 and indicate that synthetic mycolic acids suppress allergic responses in a mouse model for asthma. These are promising results for the use of these molecules as a treatment for human allergic diseases.

Example 9

Therapeutic Effects in a Mouse Asthma Model

In example 8 mycolic acid containing liposomes were administered to healthy lungs of experimentally allergic mice. In this example synthetic mycolic acids were also tested for their usefulness as a therapeutic molecule in allergic airway disease.

Figure 6:
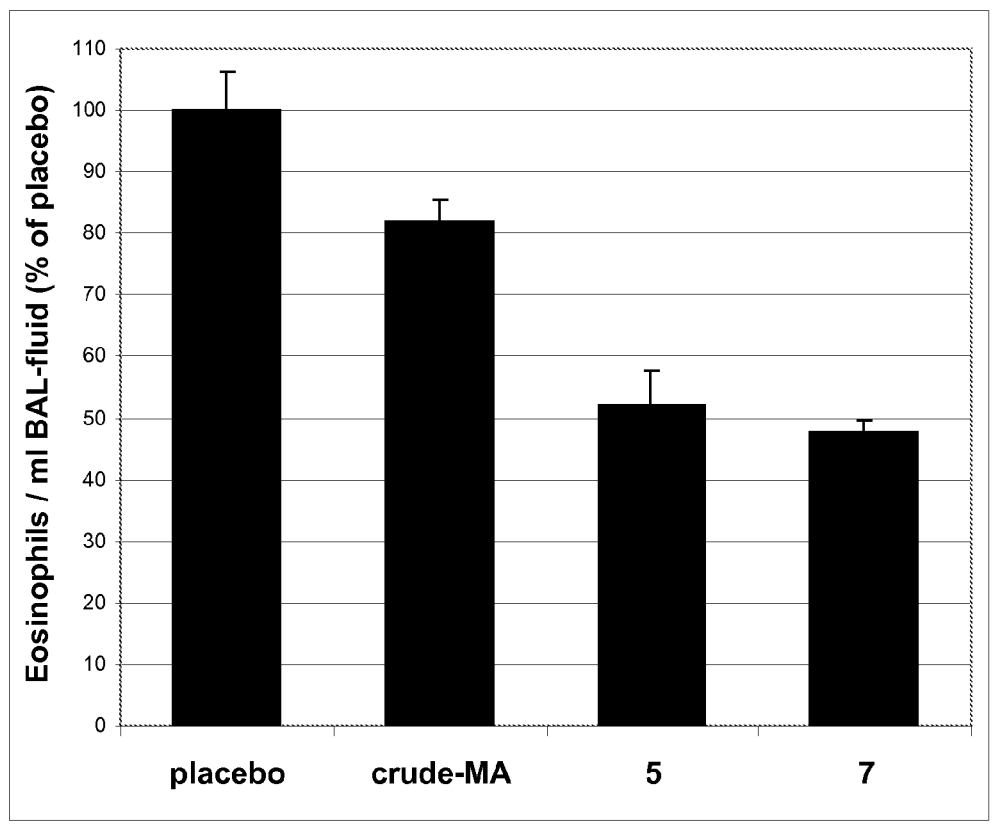
FIG. 6 depicts a histological graph of an analysis of the therapeutic efficacy of synthetic mycolic acids in mouse asthma models.
Figure 7A:
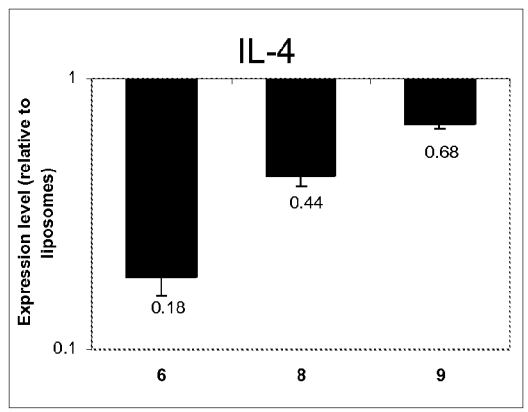
FIG. 7a, 7b, 7c, 7d and 7e each depict histological graphs of several analyses of mRNA expression patterns by RT-qPCR of CD4+ T-helper (Th) lymphocytes, isolated from asthmatic mouse lungs, which mice had been treated with certain synthetic mycolic acids.
Figure 7B:
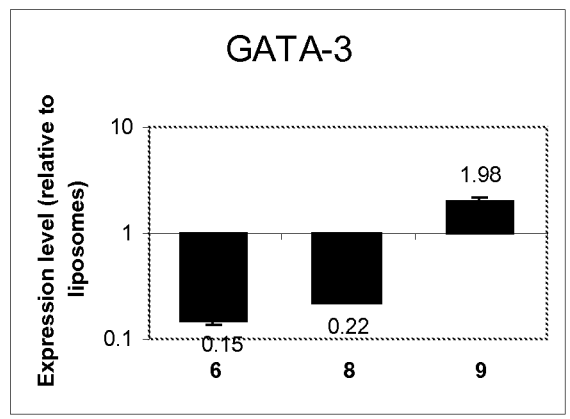
Figure 7C:
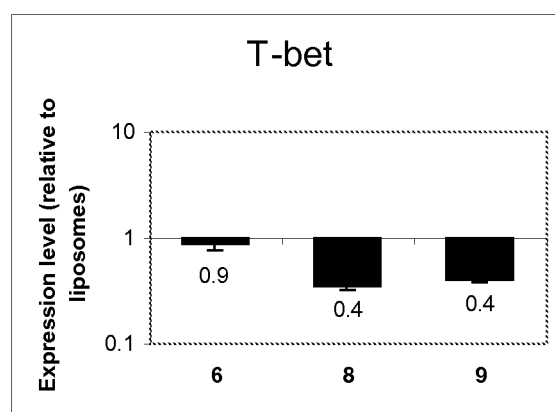
Figure 7D:
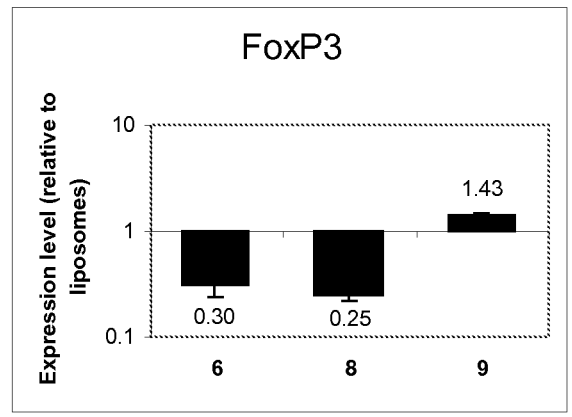
Figure 7E:
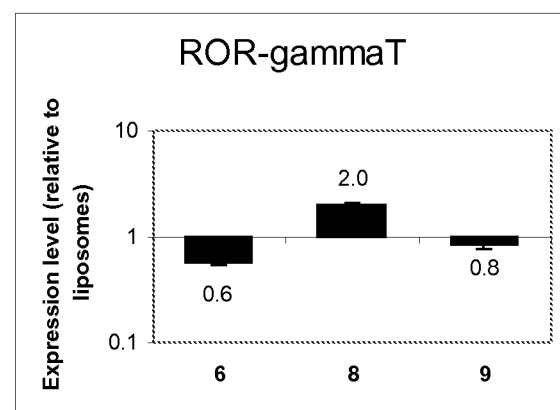

Liposomes containing mycolic acid isomers 5 and 7 were administered intratracheally to OVA-immunised mice, previously exposed to a series of OVA-aerosol challenges. The therapeutic effect of this treatment after a second series of OVA-aerosol-challenges was analysed by flowcytometric analysis of the BAL-cell numbers and compared to those of a placebo treated and a crude-MA comparative sample treated group. The placebo group were treated with phosphate buffered saline. While the crude-MA sample could only marginally suppress the allergic airway response, compounds 5 and 7 brought about an approximately 2-fold reduction of the eosinophilia. The results are shown in FIG. 6. This means that in addition to a prophylactic effect, molecules of formula I are also therapeutically active in a mouse asthma model.

As well as a reduction in the eosinophilic cell infiltrate found in the BAL-fluid of mice treated with compounds 5 and 7 and subsequently re-challenged with OVA-aerosol, the absence of blood in the lavage fluid was also observed. This was in contrast with the placebo treated mice, where easy bleeding of the lungs during the BAL is indicative for more sensitive tissue, heavily affected by the elicited immune pathology.

Example 10

Synthetic Mycolic Acids Structure Specifically Mediate Immune Modulation

From the previous examples it can be concluded that the synthetic mycolic acids have a significant effect on immune reactivity. The nature of the immune modification appears to be structure dependent. This can be seen from examination of mRNA expression patterns by RT-qPCR of CD4+ T-helper (Th) lymphocytes, isolated from asthmatic mouse lungs after treatment with compounds 6, 8 and 9 formulated into liposomes. The results are shown in FIGS. 7a to e with reference to an empty liposome treatment. All of the synthetic mycolic acid isomers repressed the transcription of the Th2 effector cytokine IL-4 to some degree. Both compound 6 and 8 are especially good in suppressing Th2 (IL-4, Gata-3) and regulatory T-cell (FoxP3) responses, but only compound 8 also interferes with the Th1/Th17 balance by up-regulationg ROR-gammaT, the Th17-restricted transcription factor. Although treatment with synthetic mycolic acid 9 resulted in an up-regulation of GATA-3 transcription, Th2-cytokine IL-4 was not induced, possibly due to a counterbalance effect by FoxP3-expressing regulatory T-cells.

The observed decrease in responsiveness of Th2 cells, a Th cell subset prominent in driving allergic inflammation, along with the absence of compensatory increases of Th17 and especially Th1 cell responses, likely is at the basis of the prophylactic and therapeutic effects of specific synthetic mycolic acid structures shown in the examples 8 and 9 respectively. Moreover, these differential effects on Th cell subsets illustrate the potential of specific synthetic mycolic acid structures to interfere with other types of diseases of the immune system.

The invention claimed is:
1. A synthetically prepared compound according to formula IIa,

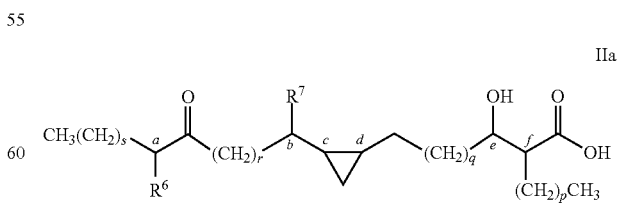

for the treatment of a disease of the immune system;
wherein
$R^6$ is hydrogen or $C_1$ to $C_4$ alkyl,
$R^7$ is hydrogen or $C_1$ to $C_4$ alkyl, p is from 16 to 30,
q is from 8 to 24,
r is from 12 to 28 and
s is from 12 to 28, and wherein at least 90% of the compound of formula IIa is provided as a single homologue, single regioisomer and/or a single stereoisomer
except for the following compounds:

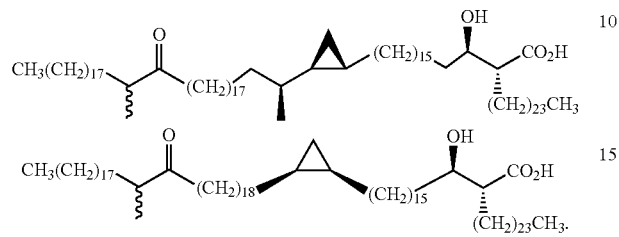

2. A composition comprising a compound of formula IIa as defined in claim 1 and a pharmaceutically acceptable carrier.

3. A composition according to claim 2 wherein the pharmaceutically acceptable carrier comprises a liposome.

* * * * *